United States Patent
Minotti et al.

(10) Patent No.: US 6,927,211 B2
(45) Date of Patent: Aug. 9, 2005

(54) METHOD FOR REDUCING TOXICITY OF COMBINED CHEMOTHERAPIES

(75) Inventors: Giorgio Minotti, Rome (IT); Luca Gianni, Milan (IT)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/728,015

(22) Filed: Dec. 4, 2003

(65) Prior Publication Data

US 2004/0077561 A1 Apr. 22, 2004

Related U.S. Application Data

(62) Division of application No. 09/954,953, filed on Sep. 18, 2001.
(60) Provisional application No. 60/234,496, filed on Sep. 22, 2000.

(51) Int. Cl.⁷ ................... A61K 31/704; A61K 31/337
(52) U.S. Cl. ............... 514/34; 514/449; 514/2; 514/365; 514/388; 514/397; 514/690; 514/269; 514/50; 536/6.4; 536/17.2; 536/18.4; 536/18.5; 536/4.1; 424/178.1; 424/145.1; 549/214; 435/69.1; 435/810
(58) Field of Search ................. 514/34, 449, 2, 514/365, 388, 397, 690, 269, 50; 536/6.4, 17.2, 18.4, 18.5, 4.1; 424/178.1, 145.1; 549/214; 435/69.1, 810

(56) References Cited

U.S. PATENT DOCUMENTS

| | | | |
|---|---|---|---|
| 4,203,900 A | 5/1980 | Kaiser | |
| 4,206,221 A | 6/1980 | Miller et al. | |
| 4,303,439 A | 12/1981 | Howe et al. | |
| 4,354,029 A | 10/1982 | Kaiser et al. | |
| 4,360,678 A | 11/1982 | Howe et al. | |
| 4,443,611 A | 4/1984 | Kaiser | |
| 4,543,414 A | 9/1985 | Carson | |
| 4,743,700 A | 5/1988 | Jamm et al. | |
| 4,814,470 A | 3/1989 | Colin et al. | |
| 4,857,653 A | 8/1989 | Colin et al. | |
| 4,876,399 A | 10/1989 | Holton et al. | |
| 4,877,881 A | 10/1989 | Belliotti et al. | |
| 4,924,002 A | 5/1990 | Kostlan | |
| 4,924,011 A | 5/1990 | Denis et al. | |
| 4,924,012 A | 5/1990 | Colin et al. | |
| 4,942,184 A | 7/1990 | Haugwitz et al. | |

(Continued)

FOREIGN PATENT DOCUMENTS

| | | |
|---|---|---|
| CA | 1061330 | 8/1979 |
| DE | 1695918 | 5/1971 |
| DE | 2919891 | 12/1980 |

(Continued)

OTHER PUBLICATIONS

Loshak. "New drug combination enhances treatment for advanced breast cancer." DG–Dispatch–ECCO, online: www.pslgroup.com/dg/12c452.html, Sep. 17, 1999, pp. 1–2.*

Donnelli, M.G., et al; Pharmacokinetics of anticancer agents in patients with impaired liver function; European Journal of Cancer; Pergamon Press; Oxford, Great Britain; vol. 34, No. 1; Jan. 1998.

ECCO: Taxol/doxorubicin Improves Survival in Metastatic Breast Cancer; Doctor's Guide, 'Online!, Sep. 22, 1999; retrieved from the Internet: www.pslgroup.com/dg/13144a.htm; retrieved Nov. 6, 2002.

(Continued)

Primary Examiner—Elli Peselev
Assistant Examiner—Devesh Khare
(74) Attorney, Agent, or Firm—Elliott Korsen; Maureen Gibbons

(57) ABSTRACT

Compositions and methods are provided for use in the treatment of cancer.

14 Claims, 6 Drawing Sheets

U.S. PATENT DOCUMENTS

| | | |
|---|---|---|
| 4,960,790 A | 10/1990 | Stella et al. |
| 5,015,744 A | 5/1991 | Holtan |
| 5,059,699 A | 10/1991 | Kingston et al. |
| 5,128,478 A | 7/1992 | Ito et al. |
| 5,136,060 A | 8/1992 | Holtan |
| 5,194,635 A | 3/1993 | Kingston et al. |
| 5,208,237 A | 5/1993 | Hewawasam et al. |
| 5,227,400 A | 7/1993 | Holton et al. |
| 5,243,045 A | 9/1993 | Holton et al. |
| 5,254,580 A | 10/1993 | Chen |
| 5,264,591 A | 11/1993 | Bombardelli et al. |
| 5,272,171 A | 12/1993 | Ueda et al. |
| 5,278,324 A | 1/1994 | Kingston et al. |
| 5,283,253 A | 2/1994 | Holton et al. |
| 5,296,506 A | 3/1994 | Kingston |
| 5,319,112 A | 6/1994 | Kingston et al. |
| 5,352,806 A | 10/1994 | Gunawardana et al. |
| 5,399,726 A | 3/1995 | Holton et al. |
| 5,420,337 A | 5/1995 | Patel et al. |
| 5,440,056 A | 8/1995 | Klein et al. |
| 5,449,790 A | 9/1995 | Zheng et al. |
| 5,468,769 A | 11/1995 | Klein et al. |
| 5,476,954 A | 12/1995 | Borzat et al. |
| 5,556,878 A | 9/1996 | Kelly et al. |
| 5,580,997 A | 12/1996 | Bouchard et al. |
| 5,589,502 A | 12/1996 | Tsujihara et al. |
| 5,616,739 A | 4/1997 | Mas et al. |
| 5,618,952 A | 4/1997 | Holton et al. |
| 5,621,121 A | 4/1997 | Cammercon et al. |
| 5,635,531 A | 6/1997 | Chen |
| 5,637,732 A | 6/1997 | Holton et al. |
| 5,646,176 A | 7/1997 | Golik et al. |
| 5,670,658 A | 9/1997 | Bastart |
| 5,677,470 A | 10/1997 | Tsujihara et al. |
| 5,710,287 A | 1/1998 | Holton et al. |
| 5,721,268 A | 2/1998 | Holton et al. |
| 5,728,687 A | 3/1998 | Bissery |
| 5,728,725 A | 3/1998 | Holton et al. |
| 5,760,252 A | 6/1998 | Holton et al. |
| 5,767,296 A | 6/1998 | Terasawa et al. |
| 5,773,461 A | 6/1998 | Wittma et al. |
| 5,808,102 A | 9/1998 | Poss et al. |
| 5,840,931 A | 11/1998 | Bouchard et al. |
| 5,847,170 A | 12/1998 | Bouchard et al. |
| 5,889,043 A | 3/1999 | Bouchard et al. |
| 5,908,835 A * | 6/1999 | Bissery .................. 514/33 |
| 6,005,120 A | 12/1999 | Holton et al. |
| 6,020,507 A | 2/2000 | Gibson |
| 6,043,375 A | 3/2000 | Borzat et al. |
| 6,072,060 A | 6/2000 | Suidell et al. |
| 6,096,909 A | 8/2000 | Ojima |
| 6,100,411 A | 8/2000 | Ojima |
| 6,214,863 B1 | 4/2001 | Bissery |
| 6,239,167 B1 | 5/2001 | Bissery |
| 6,248,908 B1 | 6/2001 | Kant |
| 6,340,701 B1 | 1/2002 | Chari et al. |
| 6,353,120 B2 | 3/2002 | Kant |

FOREIGN PATENT DOCUMENTS

| | | |
|---|---|---|
| EP | 0 359 516 B1 | 8/1994 |
| EP | 0 428 376 B1 | 1/1996 |
| EP | 0 537 905 B1 | 3/1996 |
| EP | 0 537 905 A1 | 3/1996 |
| EP | 0 505 047 B1 | 4/1996 |
| EP | 0 505 047 A1 | 4/1996 |
| EP | 0 400 971 B1 | 7/1998 |
| EP | 0 400 971 A3 | 7/1998 |
| EP | 0 604 910 A1 | 7/2004 |
| JP | 55-145650 | 11/1980 |
| JP | 60-222416 | 11/1985 |
| JP | 61-005022 | 1/1986 |
| JP | 61-115022 | 6/1986 |
| JP | 61-51578 | 11/1986 |
| JP | 9208572 A | 8/1997 |
| WO | WO 90/02738 | 3/1990 |
| WO | WO 92/09589 | 6/1992 |
| WO | WO 92/19765 | 11/1992 |
| WO | WO 94/07876 | 4/1994 |
| WO | WO 94/13655 | 6/1994 |
| WO | WO 94/14787 | 7/1994 |
| WO | WO 95/03265 | 2/1995 |
| WO | WO 96/00724 | 1/1996 |
| WO | WO 96/13495 | 5/1996 |
| WO | WO 96/14309 | 5/1996 |
| WO | WO 96/23779 | 8/1996 |
| WO | WO 97/09979 | 3/1997 |
| WO | WO 97/23472 | 7/1997 |
| WO | WO 97/32578 | 9/1997 |
| WO | WO 97/32869 | 9/1997 |
| WO | WO 98/01435 | 1/1998 |
| WO | WO 98/22451 | 5/1998 |
| WO | WO 99/33462 | 7/1999 |

OTHER PUBLICATIONS

DG Dispatch—ECCO: New Drug Combination Enhances Treatment for Advanced Breast Cancer; Doctor's Guide; 'Online!; Sep. 19, 1999; retrieved from the Internet: www.pslgroup.com/dg/12c452.htm.

Sparano, "Doxorubicin/Taxane combinations: Cardiac toxicity and pharmacokinetics." Seminars in Oncology, vol. 26, No. 3, Suppl. 9 (Jun. 1999), pp. 14–19.

Gianni et al., "Human pharmacokinetic characterization and in vitro study of the interaction between doxorubicin and paclitaxel patients with breast cancer." Journal of clinical oncology, vol. 15, No. 5 (May 1997) pp. 1906–1915.

Zoli et al. "In vitro activity of taxol and taxotere in comparison with doxorubicin and cisplatin on primary cell cultures of human breast cancers." Breast Cancer Research and Treatment, 34, 1995, pp. 63–39.

Wahl et al. "Selective tumor sensitization to taxancs with the mab–drug conjugate CBR96–doxorubicin." Abstract: Int. J. Cancer vol. 4 (Aug. 15, 2001), pp. 590–600.

* cited by examiner

\* P< 0.05 vs control

─△─ 4-desacetyl-4-methylcarbonate taxol

METHOD FOR REDUCING TOXICITY OF COMBINED CHEMOTHERAPIES

RELATED APPLICATION

This application claims the benefit under Title 35 § 119(e) of U.S. Provisional Application No. 60/234,496, filed Sep. 22, 2000. This application is a divisional of co-pending U.S. patent application Ser. No. 09/954,953 filed on Sep. 18, 2001.

FIELD OF THE INVENTION

This invention relates to the fields of oncology and improved chemotherapy regimens.

BACKGROUND OF THE INVENTION

Taxol® (paclitaxel) has been shown to have excellent antitumor activity in vivo. Taxol® has been employed in the treatment of a variety of cancers, including breast, ovarian and lung cancer.

The clinical use of doxorubicin (DOX), an anthracycline, in cancer therapy is limited by the possible development of chronic cardiomyopathy and congestive heart failure, especially when the cumulative dose exceeds about 500 mg/m$^2$. Combining DOX with paclitaxel (PTX) has been shown to cause an unacceptable incidence of cardiac events at cumulative doses of the anthracycline below about 500 mg/m$^2$. Because of such enhancement in cardiotoxicity, the cumulative dose of DOX must be reduced to about 360 mg/m$^2$ when the anthracycline is given in combination with PTX. There are reports indicating that combination therapy with docetaxel (DCT) would not increase the cardiotoxicity of DOX. It is noteworthy, however, that very few patients in these studies were exposed to cumulative doses of DOX higher than about 360–400 mg/m$^2$.

Two-electron reduction of the carbonyl group in the side chain of DOX converts the anthracycline to a dihydroxy (secondary alcohol) metabolite called doxorubicinol (DOXol). This reaction is catalyzed by NADPH oxidoreductases located in the cytosol. There is growing evidence that DOXol may be an important mediator of cardiotoxicity. One-electron reduction of the quinone moiety in the tetracyclic ring of DOX generates a semiquinone that oxidizes to regenerate the parent anthracycline by reducing oxygen to free radicals. This reaction is catalyzed by several reductases, including the microsomal NADPH cytochrome P-450 reductase and the mitochondrial NADH dehydrogenase. The role of free radicals in anthracycline-induced cardiotoxicity is controversial, but these species may play a more definite role when synergized by the concomitant formation of DOXol.

As those experienced in the field of oncology appreciate, a need exists for combination chemotherapy regimens having improved efficacy and safety.

SUMMARY OF THE INVENTION

In accordance with the present invention, a method for the treatment of cancer is provided comprising administration of 4-desacetyl-4-methylcarbonate taxol and doxorubicin to a patient in need thereof. Surprisingly, it has been found that 4-desacetyl-4-methylcarbonate taxol does not stimulate formation of cardiotoxic metabolic doxorubicin by-products. In one embodiment of the invention, the 4-desacetyl-4-methylcarbonate taxol and doxorubicin are administered to a patient sequentially in any order. In an alternative embodiment, the 4-desacetyl-4-methylcarbonate taxol and doxorubicin are administered concomitantly. Preferably, the agents are administered sequentially with doxorubicin being administered first.

Also provided with the present invention is a chemotherapeutic composition comprising a chemotherapeutically effective amount of 4-desacetyl-4-methylcarbonate taxol and doxorubicin. In a further embodiment of the invention, the chemotherapeutic composition is disposed within a pharmaceutically acceptable carrier. Alternatively, each agent, 4-desacetyl-4-methylcarbonate taxol and doxorubicin may be formulated separately to facilitate sequential administration of the compositions.

The pharmaceutical compositions may be administered by any route and in any amount suitable to obtain the desired anti-cancer effect. In one embodiment, 4-desacetyl-4-methylcarbonate taxol and doxorubicin are separately infused into a patient with an interval between infusions ranging from about 30 minutes to 24 hours with about a one hour interval being preferred. Intravenous administration of the agents is also preferred.

DETAILED DESCRIPTION OF THE INVENTION

Figure 1:
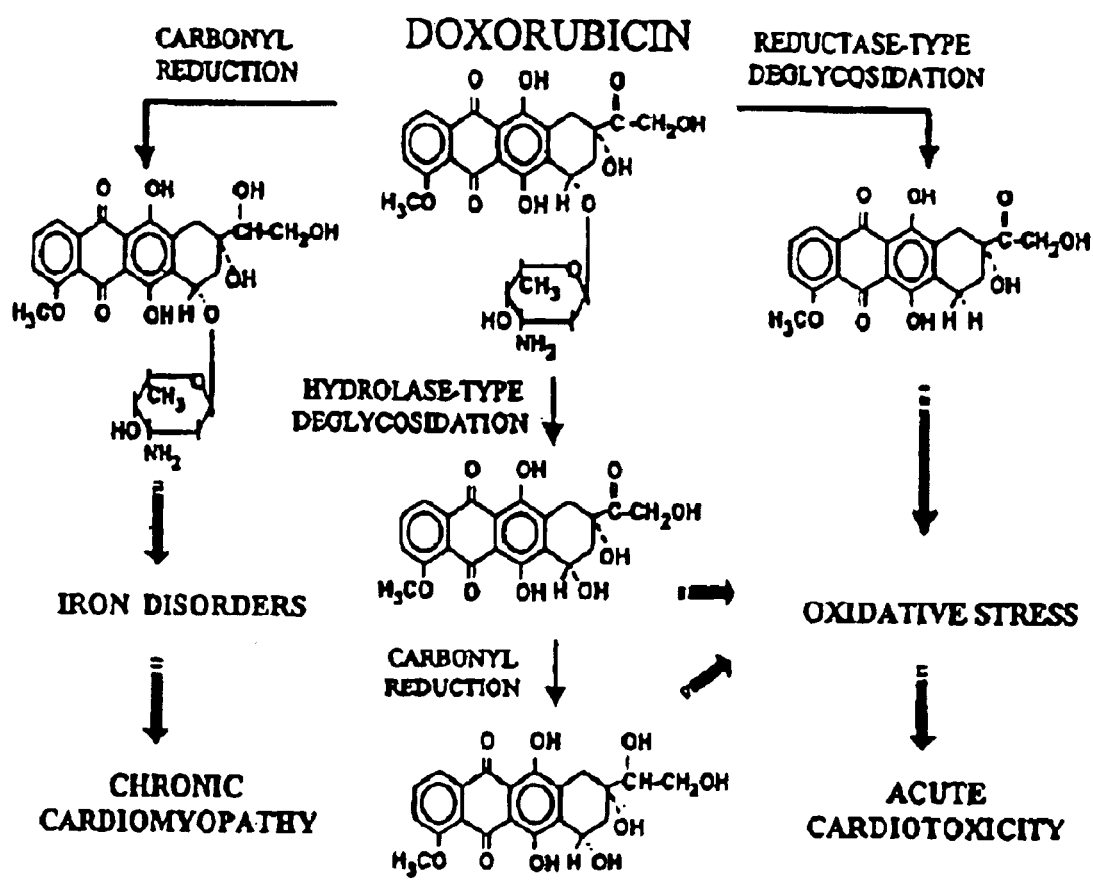
FIG. 1 is a schematic diagram showing the metabolic conversion of doxorubicin to toxic by-products.
Figure 2A:
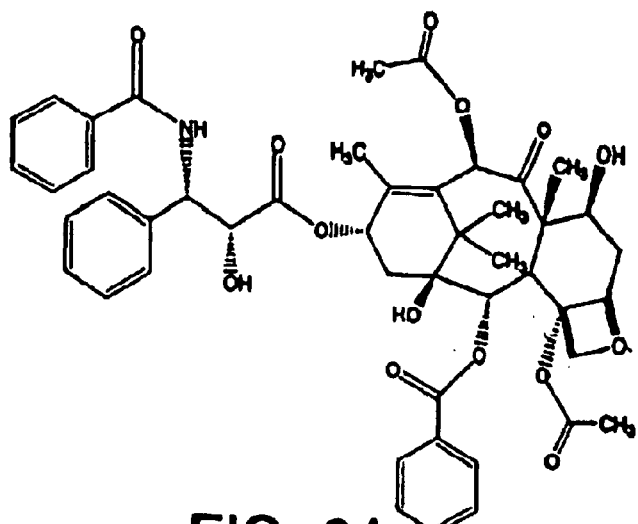
FIGS. 2A–2C depict the structures of paclitaxel (PTX) (FIG. 2A); docetaxel (DCT) (FIG. 2B) and 4-desacetyl-4-methylcarbonate taxol (FIG. 2C).
Figure 2B:
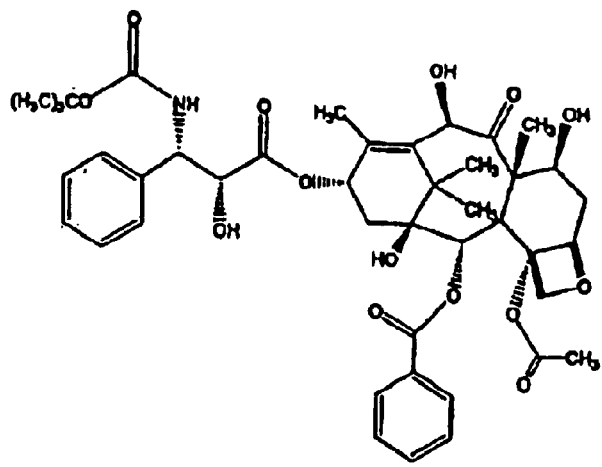
Figure 2C:
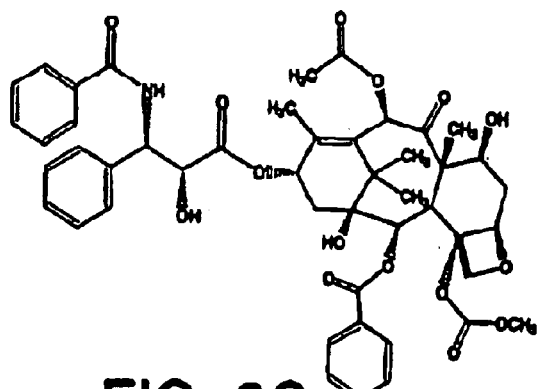

A systematic study was undertaken to characterize whether 4-desacetyl-4-methylcarbonate taxol increases DOXol and free radicals in the heart. Side-by-side comparisons of PTX, DCT and 4-desacetyl-4-methylcarbonate taxol were made. Studies have shown that a dose-related incidence of doxorubicin (DOX)-induced cardiotoxicity is increased by paclitaxel (PTX) but not docetaxel (DCT). It is possible however, that the reduced cardiotoxic effects of DOX-DCT combinations may be due to administration of lower cumulative doses of DOX. To characterize mechanisms and analogue-specificity of DOX-taxane interactions, an evaluation was undertaken to assess the effects of PTX, DCT and a new taxane 4-desacetyl-4-methylcarbonate taxol, on the metabolic conversion of DOX to toxic species in human myocardium. DOX metabolism was assessed in subcellular fractions of myocardial samples disposed of during aorto-coronary by-pass grafting. The formation of DOX metabolites which mediate the acute and chronic phases of cardiotoxicity (oxygen free radicals, the aglyconic alcohol metabolite doxorubicinolone, and the glycosidic alcohol metabolite doxorubicinol, respectively) were measured. PTX and DCT (1 $\mu$M) increase the cytoplasmic conversion of DOX and doxorubicinone to doxorubicinol and doxorubicinolone, respectively [doxorubicinol: from 0.46±0.04 to 1.1±0.2 and 1.2±0.2 nmol/mg prot./4h; doxorubicinolone: from 0.8±0.1 to 1.4±0.2 and 1.3±0.2 nmol/mg prot./4h; n=3, P<0.05). PTX and DCT (10 $\mu$M) also increase the redox cycling of DOX with oxygen and the consequent generation of superoxide anion radicals in microsomal fractions (from 1.6±0.1 to 2.2±0.2 and 2.4±0.2 nmol/mg prot./min, respectively; n=4-10, P<0.05). Under comparable conditions 4-desacetyl-4-methylcarbonate taxol did not increase the formation of doxorubicinol, doxorubicinolone or superoxide anion radicals. As described herein, the commercially available taxanes PTX and DCT, but not 4-desacetyl-4-methylcarbonate taxol, share the potential to increase levels of toxic DOX metabolites in human myocardium. While recommending cardiac surveillance in patients treated with DOX and PTX or DCT, these findings suggest less cardiotoxic potential when combining 4-desacetyl-4-methylcarbonate taxol with DOX. Advantageously, a higher cumulative dose of doxorubicin may be used in combination with 4-desacetyl-4-methylcarbonate taxol as compared to combinations of doxorubicin with PTX or DCT.

The enzymes of DOX metabolism are strongly species-related. To avoid the potential pitfalls associated with studies in animal models, an in vitro human heart assay was utilized. The assay involves isolation of both cytosolic fractions generating DOXol, and microsomal fractions converting DOX to free radicals.

Materials and methods for synthesizing 4-desacetyl-4-methylcarbonate taxol are provided in PCT/US93/12173 and EP 0604910B1, the entire disclosure of each of the above-identified patent applications being incorporated by reference herein. Pharmaceutically acceptable salts of 4-desacetyl-4-methylcarbonate taxol which also have reduced ability to stimulate formation of cardiotoxic by-products are within the scope of the present invention. Such salts, including but not limited to, the hydrochloride or sodium salts, may be prepared following procedures which are familiar to those skilled in the art.

Methods for the administration of the chemotherapeutic agents of the invention are also disclosed. Doxorubicin and 4-desacetyl-4-methylcarbonate taxol may be administered to a patient simultaneously, or they may be administered sequentially in any order. In a preferred embodiment, the anthracycline, doxorubicin, is administered initially. After approximately a period of about 30 minutes to 24 hours, 4-desacetyl-4-methylcarbonate taxol is administered. Dosages suitable for administration of the chemotherapeutic compositions of the invention are set forth hereinbelow.

Whether administered sequentially or concomitantly, the compositions may be administered in any amount or by any route of administration effective for the treatment of cancer. Thus, the expression "chemotherapeutically effective amount", as used herein, refers to a sufficient amount of the compounds of the invention to provide the desired anti-cancer effect. The exact amount required will vary from subject to subject, the mode of administration of the chemotherapeutic compounds and the like.

The present invention further provides chemotherapeutic compositions comprising both 4-desacetyl-4-methylcarbonate taxol and doxorubicin. Alternatively, the chemotherapeutic pharmaceutical compositions of the present invention comprise one of the above-described compounds as the active ingredient, in combination with a pharmaceutically acceptable carrier medium or an auxiliary agent. Thus, in this embodiment, the 4-desacetyl-4-methylcarbonate taxol and the doxorubicin are formulated separately.

The compositions of the pharmaceuticals of the invention may be prepared in various forms for administration, including tablets, caplets, pills, or dragees, or can be filled in suitable containers, such as capsules, or, in the case of suspensions, filled into bottles. As used herein, "pharmaceutically acceptable carrier medium" includes any and all solvents, diluents, other liquid vehicle, dispersion or suspension aids, surface active ingredients, preservatives, solid binders, lubricants, and the like, as suited to the particular dosage form desired. *Remington's Pharmaceutical Sciences*, Fifteenth Edition, E. W. Martin (Mack Publishing Co., Easton Pa. 1975) discloses various vehicles or carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of the invention.

In the pharmaceutical combination compositions of the invention, the active agents may be present in an amount of at least about 0.1% and not more than about 95% by weight, based on the total weight of the compositions, including carrier medium and auxiliary agent(s). Preferably, the proportion of active agent varies between about 1% and about 75% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The chemotherapeutic compositions described herein are preferably formulated in dosage unit form for ease of administration and uniformity of dosage. "Dosage unit form" as used herein refers to a physically discrete unit of chemotherapeutic composition for the patient to be treated. Each dosage should contain the quantity of active material calculated to produce the desired therapeutic effect either as such, or in association with the selected pharmaceutical carrier medium. Typically, the anthracyclines, including doxorubicin, are administered in dosage units ranging between about 40 mg to about 200 mg of the agent, with a range of about 40–150 mg being preferred. Typically, the taxanes, including 4-desacetyl-4-methylcarbonate taxol are administered in dosage units ranging between about 50–380 mg of the agent, with a range of about 50 mg to 300 mg being preferred. The chemotherapeutic combination compositions of the invention may be administered orally, parenterally, by intramuscular injection, intraperitoneal injection, intravenous infusion, or the like. Intravenous administration is particularly preferred. The chemotherapeutic compositions of the invention are typically administered by intravenous infusions of varying duration, with infusions of 1 hour to 24 hours being preferred.

The chemotherapeutic compositions may be administered one or more times every month to obtain the desired therapeutic effect. In a preferred embodiment of the present invention, the chemotherapeutic agents are sequentially administered by intravenous infusions, with doxorubicin being preferably administered first. Different intervals between administration of the compounds may be selected. Such intervals may range between about 30 minutes and 24 hours, with 1 hour being preferred.

Biological studies of combination chemotherapeutic regimens have been performed in cardiac cellular fractions. Surprisingly, it has been discovered that 4-desacetyl-4-methylcarbonate taxol does not stimulate production of cardiotoxic metabolites and by-products of doxorubicin when incubated with the anthracycline in human cardiac cytosol. The test procedures and results of these studies are set forth below.

Reconstitution of DOX Metabolism and DOXol Formation, Plus or Minus Taxanes, in Human Cardiac Cytosol.

Human myocardium is obtained from patients undergoing aorto-coronary bypass grafting. All samples were routinely disposed of by the surgeons from the lateral aspect of excluded right atrium during cannulation procedures for cardio-pulmonary by-pass. After storage at −80° C., pools of 15–20 samples are processed for cytosol preparation by sequential homogenization, ultracentrifugation and overnight 65% ammonium sulfate precipitation of 105,000 g supernatants. Next, cytosol is dialyzed against 100 mM Tris HCl-40 mM KCl, pH 8.9, diluted to 3 mg protein/ml with the same buffer, and incubated for 15 minutes at room temperature with 100 mM dithiothreitol to promote non-denaturing disassembly of the [4Fe-4S] cluster of cytoplasmic aconitase. This treatment is necessary as reactions of DOXol with [4Fe-4S] clusters would convert this metabolite back to DOX. Sizable amounts of DOXol would therefore go undetected if they reacted with [4Fe-4S] clusters prior to their assay. Unreacted dithiothreitol was eventually removed by sequential gel filtration on (1.5×10 cm) Sepharose 6B columns, protein reprecipitation with 65% ammonium sulfate, and extensive dialysis against 0.3 M NaCl, pH 7.0. Doxorubicin metabolism was reconstituted in 0.5 ml incubations containing cytosol (0.15 mg protein), NADPH (100 $\mu$M) and DOX (25 $\mu$M), in 0.3 M NaCl (pH 7.0) 37° C. Where indicated ethanol-dissolved taxanes (1–50 $\mu$M) were included. Aliquots of taxane-free ethanol (5 $\mu$l) were included as appropriate to adjust the final volume to 10 $\mu$l in all incubations. After 4 h DOX and DOXol were extracted with 2 ml of $CHCl_3/CH_3OH$ (1:1) and separated by previously validated two-dimensional TLC on (20×20 cm) 0.25 mM F524 Silica Gel Plates, using $CHCl_3/CH_3OH/CH_3COOH/H_2O$ (80:20:14:6) as mobile phase in either dimension. Doxorubicinol was identified by cochromatography with (S)-DOXol from Streptomyces peucetius or (S) (R)-DOXol purified after $NaBH_4$ reduction of DOX. Where indicated incubations were prepared by replacing DOX with DOX aglycone and by measuring formation of DOXol aglycone. The latter was separated from DOX aglycone by using $CHCl_3/CH_3OH/CH_3COOH$ (100:2:5) and $CH_3COOC_2H_5—CH_3CH_2OH—CH_3COOH—H_2O$ (80:10:5:5) in the first and second dimension, respectively. DOX aglycone was purified after thermoacid hydrolysis of DOX.

Reconstitution of DOX Metabolism and Free Radical Formation, Plus or Minus Taxanes, in Human Cardiac Microsomes.

105,000 g pellets from human myocardium homogenates are solubilized with deoxycolate and reconstituted at the final concentration of 0.025 mg prot/ml with 10 $\mu$M DOX, 1–10 $\mu$M taxane, 0.1 mM NADPH, in 0.3 M NaCl, pH 7.0, 37° C.

Electron flow from NADPH cytochrome P-450 reductase to the quinone moiety of DOX is detected by monitoring NADPH oxidation. Redox coupling of the semiquinone with oxygen is detected by monitoring formation of the superoxide anion radical with the superoxide dismutase-inhibitable reduction of cytochrome c (25 $\mu$M). These assays are performed in a Hewlett Packard 8453A UV/VIS/NIR spectrometer equipped with computer-assisted corrections for scatter and turbidity.

EXAMPLE 1

PTX and DCT Stimulate Formation of Toxic Doxorubicin Metabolites

Figure 3:
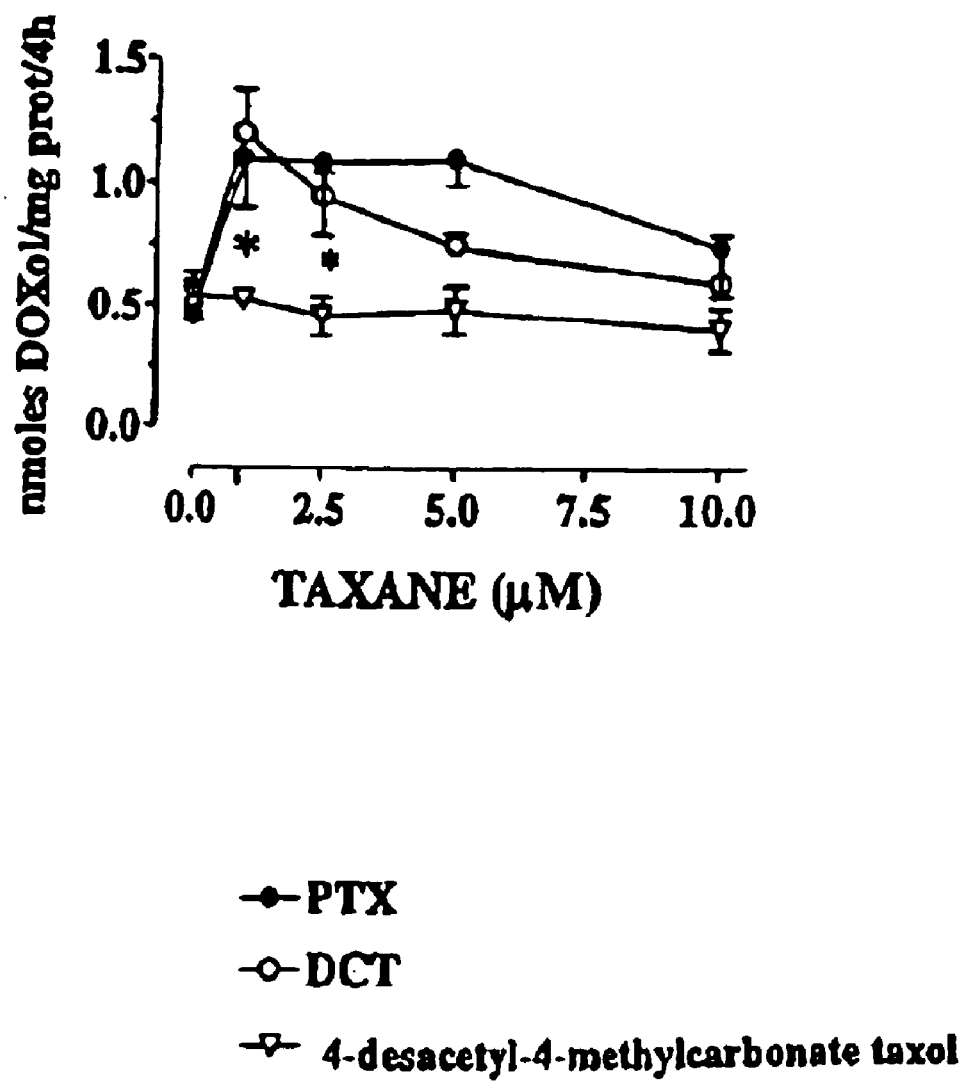
FIG. 3 is a graph showing that PTX and DCT stimulate DOXol formation in cardiac cytosol. 4-desacetyl-4-methylcarbonate taxol did not stimulate DOXol production at the concentrations tested. ∴ P=<0.05.

Both PTX and DCT stimulate DOXol formation in [4Fe-4S]-depleted human cardiac cytosol. As shown in FIG. 3, the concentration-response curves were bell-shaped, suggesting that taxanes can act as allosteric modulators of anthracycline reductases. The range of concentrations permissive to stimulation tends to be broader in the case of PTX; however, maximal stimulation by the two taxanes is identical in this set of experiments. 4-desacetyl-4-methylcarbonate taxol did not stimulate DOXol formation at any of the concentrations tested.

Figure 4A:
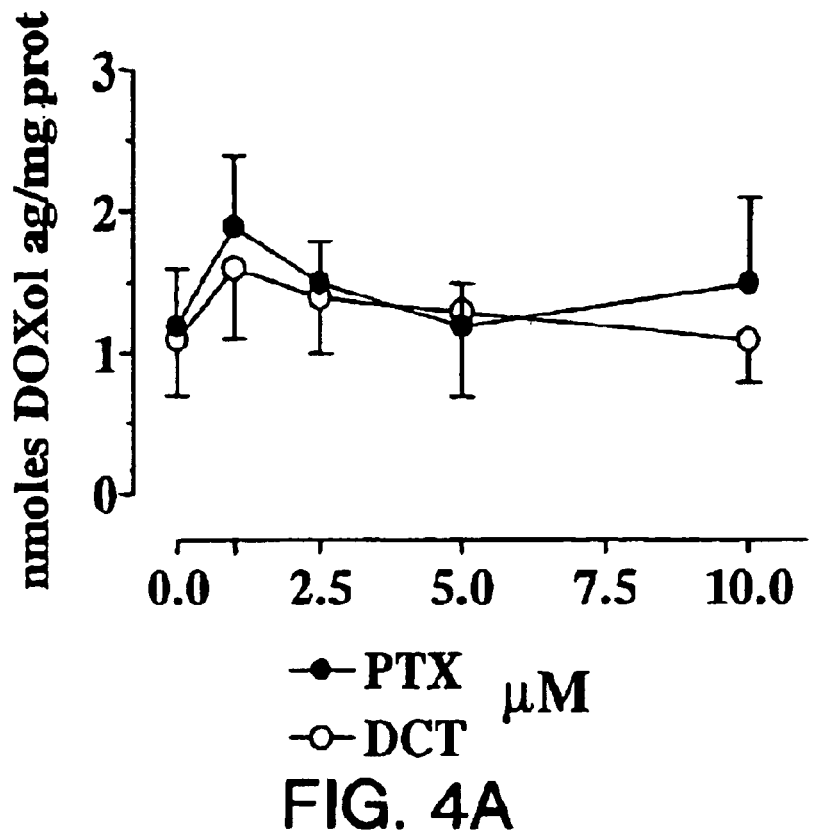
FIGS. 4A and 4B are graphs showing that PTX and DCT stimulate conversion of doxorubicinone (DOX aglycone hereafter) into doxorubicinolone (DOXol aglycone hereafter) (FIG. 4A). 4-desacetyl-4-methylcarbonate taxol failed to stimulate this conversion (FIG. 4B). ∴ P=<0.025 vs. control.
Figure 4B:
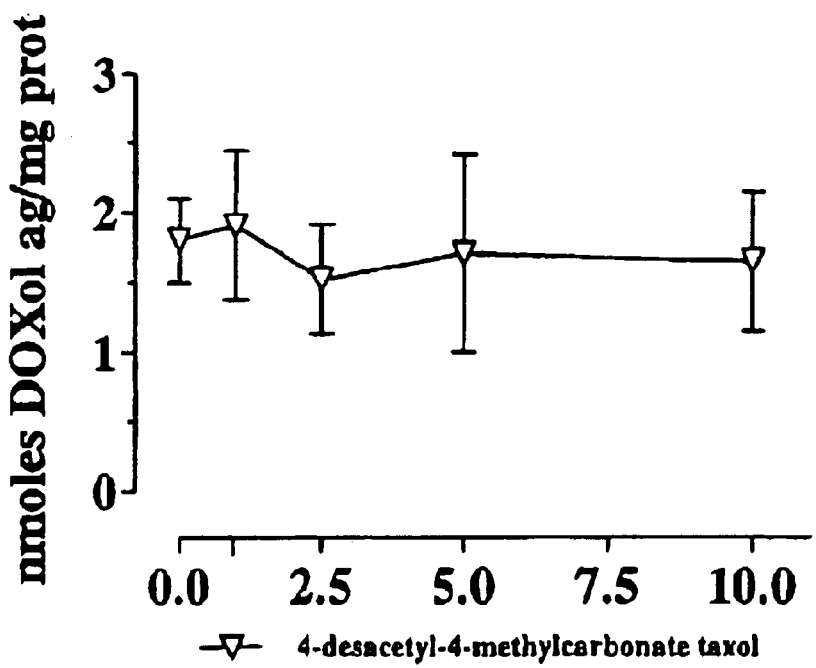

As shown in FIG. 4, PTX and DCT were also able to stimulate the conversion of DOX aglycone into DOXol aglycone. Again, the concentration-response curves were bell-shaped, the two taxanes being virtually identical with respect to both the net stimulation achievable and the range of concentrations permissive to such stimulation (Panel A). 4-desacetyl-4-methylcarbonate taxol has not been found to stimulate the formation of DOXol aglycone from DOX aglycone (Panel B).

EXAMPLE 2

Stimulation of NADPH Oxidation by Taxanes

Figure 5A:
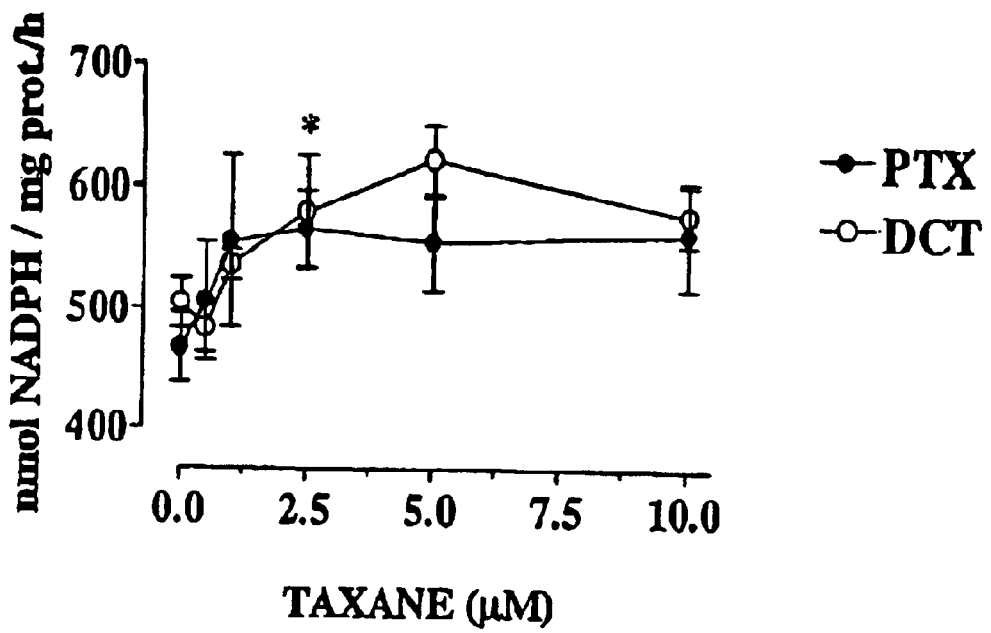
FIGS. 5A and 5B are graphs showing that both PTX and DCT stimulate NADPH oxidation by deoxycholate-solubilized microsomes isolated from the human heart when incubated with DOX (FIG. 5A). 4-desacetyl-4-methylcarbonate taxol stimulated this oxidation only at the highest levels tested (FIG. 5B). ∴ P=<0.05 versus control.
Figure 5B:
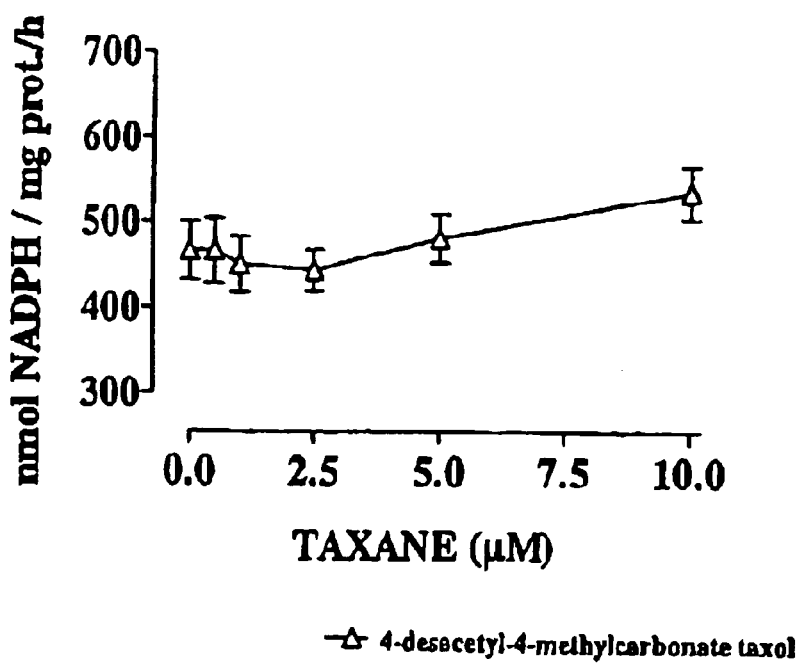

PTX and DCT were able to stimulate NADPH oxidation by deoxycolate-solubilized microsomes of human heart incubated with DOX. In this system the concentration-response curves were not bell shaped, but the stimulation increased until it reached a plateau (FIG. 5A). 4-desacetyl-4-methylcarbonate taxol stimulated NADPH oxidation only at the highest concentration tested, although this was not statistically significant. (FIG. 5B). None of the taxanes tested affected NADPH oxidation in the absence of DOX.

Figure 6:
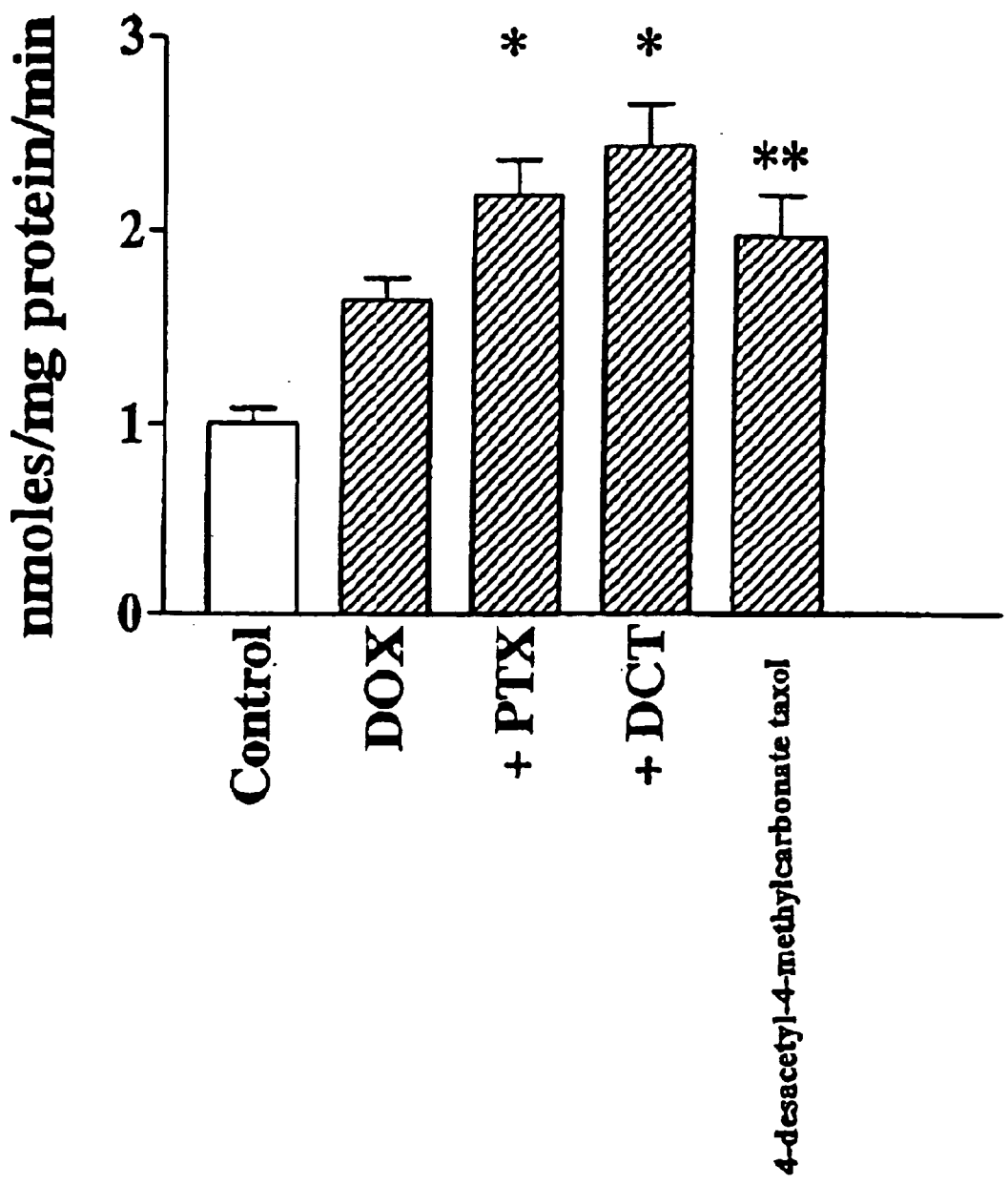
FIG. 6 is a graph showing that DOX enhances superoxide anion formation. Inclusion of 10 μM PTX or DCT resulted in a significant increase in superoxide anion formation whereas the 4-desacetyl-4-methylcarbonate taxol did not. ∴ P=<0.025 versus DOX; ∴ ∴ P=NS versus DOX.

As shown in FIG. 6, DOX was able to enhance superoxide anion formation by deoxycolate-solubilized microsomes, consistent with its ability to shunt electrons from NADPH cytochrome P-450 reductase to molecular oxygen via reduction-oxidation of its quinone moiety. The inclusion of 10 $\mu$M PTX or DCT resulted in a significant increase in superoxide formation, that was consistent with the ability of these two taxanes to stimulate NADPH oxidation under comparable conditions. Again, 4-desacetyl-4-methylcarbonate taxol did not afford any significant stimulation in these settings, which was consistent with the lack of significant effect on NADPH oxidation.

The results presented herein indicate that both PTX and DCT stimulate DOX metabolism in the human heart, resulting in increased formation of potentially cardiotoxic DOXol, DOXol aglycone, and oxygen free radicals like the superoxide anion. These findings provide molecular correlates to explain the increased cardiotoxicity of DOX-PTX combinations, and suggest that enhanced cardiotoxicity might occur also after DOX-DCT regimens if the cumulative dose of DOX were increased above about 360–400 mg/m². In contrast, 4-desacetyl-4-methylcarbonate taxol appears to lack this effect on DOX metabolism. Accordingly, 4-desacetyl-4-methylcarbonate taxol provides a superior taxane for use in combined chemotherapy regimens with DOX.

REFERENCES

Gehl J, Boesgaard M, Paaske T, Vittrup Jensen B. Dombernowsky P. *Combined doxorubicin and paclitaxel in advanced breast cancer: effective and cardiotoxic.* Ann Oncol 1996; 7: 687–93.

Gianni L, Munzone E, Capri G, Fulfaro F, Tarenzi E, Villani F et al. *Paclitaxel by 3-hour infusion in combination with bolus doxorubicin in women with untreated metastatic breast cancer: high antitumor efficacy and cardiac effects in a dose-finding and sequence-finding study* J Clin Oncol 1995; 13:2688–99.

Gianni L, Dombernowsky P, Sledge G, Amadori G, Martin M, Baynes R et al. *Cardiac function following combination therapy with Taxol7 and Doxorubicin for advanced breast cancer.* Proc Annu Meet Am Soc Clin Oncol 1998; 17:115a (abstract 444).

Nabholtz J M, Smylie M, Mackey J R, Noel D, Paterson A H, al-Tweigeri T et al. *Docetaxel/doxorubicin/cyclophosphamide in the treatment of metastatic breast cancer.* Oncology 1997; 11 (Suppl 8): 37–41.

Olson R D, Mushlin P S. *Doxorubicin cardiotoxicity: analysis of prevailing hypotheses.* FASEB J 1990; 4: 3076–86.

Minotti G, Cairo G, Monti E. *Role of iron in anthracycline cardiotoxicity: new tunes for an old song?* FASEB J 1999; 13: 199–212.

Boucek R J Jr, Olson R D, Brenner D E, Ogumbumni M E, Inui M, Fleischer S. *The major metabolite of doxorubicin is a potent inhibitor of membrane-associated ion pumps: a correlative study of cardiac muscle with isolated membrane fractions.* J Biol Chem 1987; 262 : 15851–56.

Minotti G, Recalcati S, Liberi G, Calafiore A M, Mancuso C, Preziosi P et al. *The secondary alcohol metabolite of doxorubicin irreversibly inactivates aconitase/iron regulatory protein-1 in cytosolic fractions from human myocardium.* FASEB J 1998; 12 : 541–51.

Minotti G, Cavaliere A F, Mordente A, Rossi M, Schiavello R, Zamparelli R. et al. *Secondary alcohol metabolites mediate iron delocalization in cytosolic fractions of myocardial biopsies exposed to anticancer anthracyclines.* J Clin Invest 1995; 95 : 1595–1605.

Powis G. *Free radical formation by antitumor quinones.* Free Radic Biol Med 1989; 6 : 63–101.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for the treatment of cancer, said method comprising administration of 4-desacetyl-4-methylcarbonate taxol and doxorubicin to a patient in need thereof.

2. The method as claimed in claim 1, wherein said 4-desacetyl-4-methylcarbonate taxol and doxorubicin are administered sequentially.

3. The method as claimed in claim 1, wherein said 4-desacetyl-4-methylcarbonate taxol and doxorubicin are administered simultaneously.

4. The method as claimed in claim 2, wherein said doxorubicin is administered initially followed by administration of 4-desacetyl-4-methylcarbonate taxol.

5. The method as claimed in claim 2, wherein said 4-desacetyl-4-methylcarbonate taxol is administered initially followed by administration of doxorubicin.

6. The method as claimed in claim 1, wherein said doxorubicin is administered in a dosage unit ranging between about 40–200 mg.

7. The method as claimed in claim 1, wherein said doxorubicin is administered in a dosage unit ranging between about 40–150 mg.

8. The method as claimed in claim 1, wherein said 4-desacetyl-4-methylcarbonate taxol is administered in a dosage unit ranging from between about 50–380 mg.

9. The method as claimed in claim 1, wherein said 4-desacetyl-4-methylcarbonate taxol is administered in a dosage unit ranging from between about 50–300 mg.

10. The method as claimed in claim 1, wherein said 4-desacetyl-4-methylcarbonate taxol and doxorubicin are sequentially infused into a patient and the interval between infusions ranges between about 30 minutes to about 24 hours.

11. The method as claimed in claim 1, wherein said 4-desacetyl-4-methylcarbonate taxol and doxorubicin are sequentially infused into a patient and the interval between infusions is about one hour.

12. The method as claimed in claim 1, wherein said 4-desacetyl-4-methylcarbonate taxol and doxorubicin are administered via an administration means selected from the group consisting of intravenous administration, intramuscular administration, intraperitoneal injection and oral administration.

13. The method as claimed in claim 1, wherein said 4-desacetyl-4-methylcarbonate taxol and doxorubicin are administered intravenously.

14. The method as claimed in claim 1, wherein said cancer is selected from the group consisting of breast cancer, ovarian cancer and lung cancer.

\* \* \* \* \*